(12) United States Patent
Fini et al.

(10) Patent No.: US 9,539,387 B2
(45) Date of Patent: Jan. 10, 2017

(54) INSERT AND VIAL FOR THE INFUSION OF LIQUIDS

(75) Inventors: Massimo Fini, Mirandola (IT); Alain Veneroni, Spino d'Adda (IT); Wolfgang Wehmeyer, Tubingen (DE); Wolfgang Hofmann, Frankfurt (DE)

(73) Assignee: FRESENIUS MEDICAL CARE DEUTSCHALND GMBH, Bad Homburg (DE)

( * ) Notice: Subject to any disclaimer, the term of this patent is extended or adjusted under 35 U.S.C. 154(b) by 751 days.

(21) Appl. No.: 13/992,882

(22) PCT Filed: Dec. 1, 2011

(86) PCT No.: PCT/EP2011/071452
§ 371 (c)(1),
(2), (4) Date: Jun. 10, 2013

(87) PCT Pub. No.: WO2012/076386
PCT Pub. Date: Jun. 14, 2012

(65) Prior Publication Data
US 2013/0255834 A1    Oct. 3, 2013

Related U.S. Application Data

(60) Provisional application No. 61/457,024, filed on Dec. 10, 2010.

(30) Foreign Application Priority Data

Dec. 10, 2010   (EP) .................................... 10194465

(51) Int. Cl.
*A61M 5/162*     (2006.01)
*A61J 1/14*      (2006.01)
(Continued)

(52) U.S. Cl.
CPC ............. *A61M 5/162* (2013.01); *A61J 1/1406* (2013.01); *A61J 1/20* (2013.01); *B65B 3/003* (2013.01);
(Continued)

(58) Field of Classification Search
CPC ........ A61J 1/201; A61J 1/2065; A61J 1/2072; A61M 2039/1077; A61M 5/162
(Continued)

(56) References Cited

U.S. PATENT DOCUMENTS 4,270,725 A    6/1981   Scott et al.
4,759,756 A *  7/1988   Forman ................. A61J 1/2089
                                                    604/413
(Continued)

FOREIGN PATENT DOCUMENTS

EP    0570939    11/1993
EP    1731185    2/2009
(Continued)

*Primary Examiner* — Timothy L Maust
*Assistant Examiner* — Timothy P Kelly
(74) *Attorney, Agent, or Firm* — Jacobson Holman, PLLC.

(57) ABSTRACT

The invention relates to an insert and a vial for the infusion of a liquid. The vial comprises a hollow body, a grasp portion and a head. The head comprises a delivery opening defining an axis X; a septum for closing the opening; and at least one circumferential push surface next to the head and firmly connected to the grasp portion. The insert is suitable to deliver the liquid and to receive the vial along axis X. The insert comprises a main body with lower ducts, an inner part and a piercing spike. The inner part defines a seat for the vial head, and comprises one slit for engaging the circumferential push surface. The spike is suitable to pierce the vial septum and defines upper ducts. The inner part is able to rotate inside the main body between a fluidly open configuration and a fluidly closed configuration.

14 Claims, 10 Drawing Sheets

(51) Int. Cl.
*A61J 1/20* (2006.01)
*B65B 3/00* (2006.01)

(52) U.S. Cl.
CPC ............ *A61J 1/2031* (2015.05); *A61J 1/2065* (2015.05); *A61J 1/2089* (2013.01)

(58) Field of Classification Search
USPC .................................. 141/329–330; 604/411
See application file for complete search history.

(56) References Cited

U.S. PATENT DOCUMENTS

| | | | |
|---|---|---|---|
| 5,647,845 | A | 7/1997 | Haber et al. |
| 5,762,646 | A | 6/1998 | Cotter |
| 2003/0023226 | A1 | 1/2003 | Lopez |
| 2009/0218363 | A1 | 9/2009 | Terzini |
| 2009/0255895 | A1 | 10/2009 | Kichne |
| 2011/0178493 | A1* | 7/2011 | Okiyama ............... A61J 1/2089 604/406 |

FOREIGN PATENT DOCUMENTS

| | | |
|---|---|---|
| EP | 2319553 | 5/2011 |
| EP | 2386324 | 11/2011 |
| JP | 08-238300 | 9/1996 |
| JP | 11-047273 | 2/1999 |
| JP | 2000-281114 | 10/2000 |
| WO | WO 86/01712 | 3/1986 |
| WO | WO 01/49361 | 7/2001 |
| WO | WO 2007/149960 | 12/2007 |
| WO | WO 2010/146506 | 12/2010 |
| WO | WO 2011/054693 | 5/2011 |

* cited by examiner

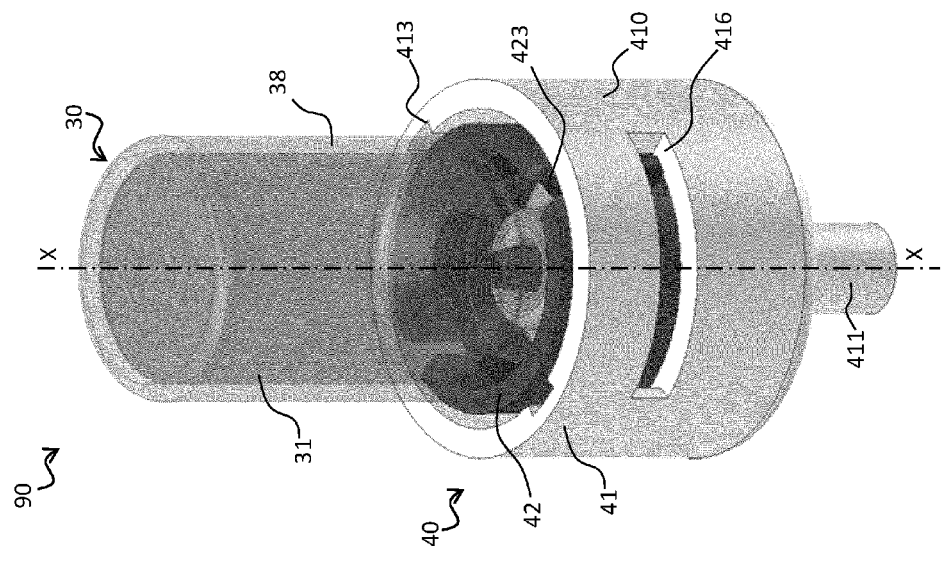
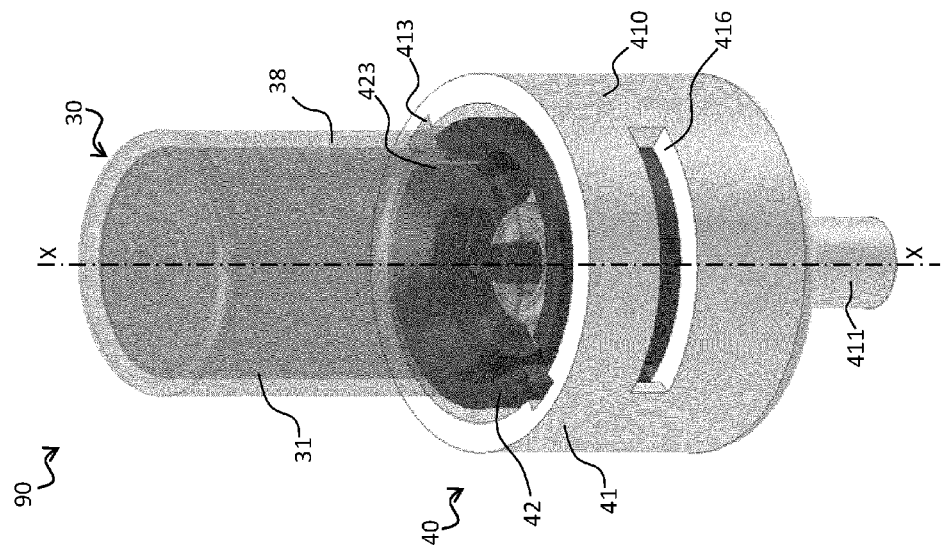

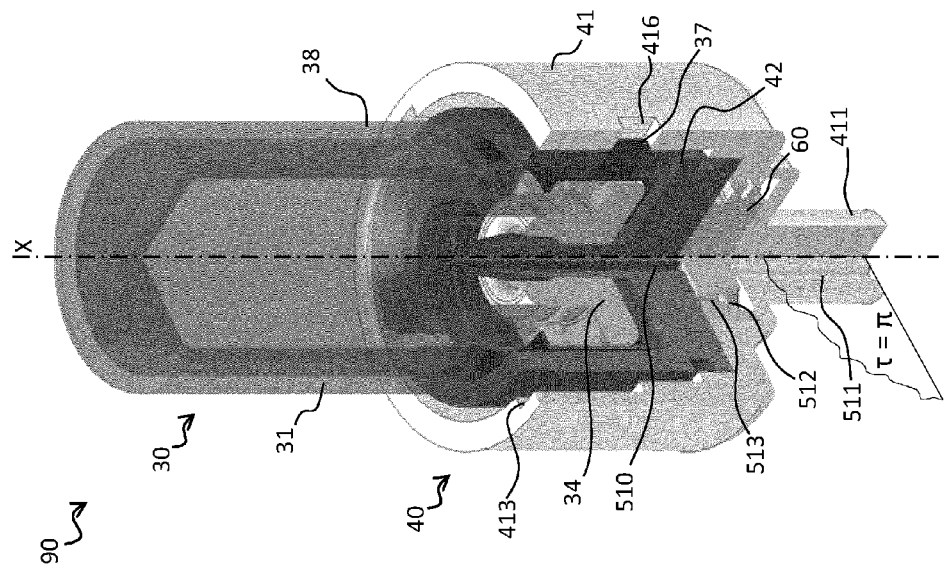
Fig. 12.a
Fig. 12.b
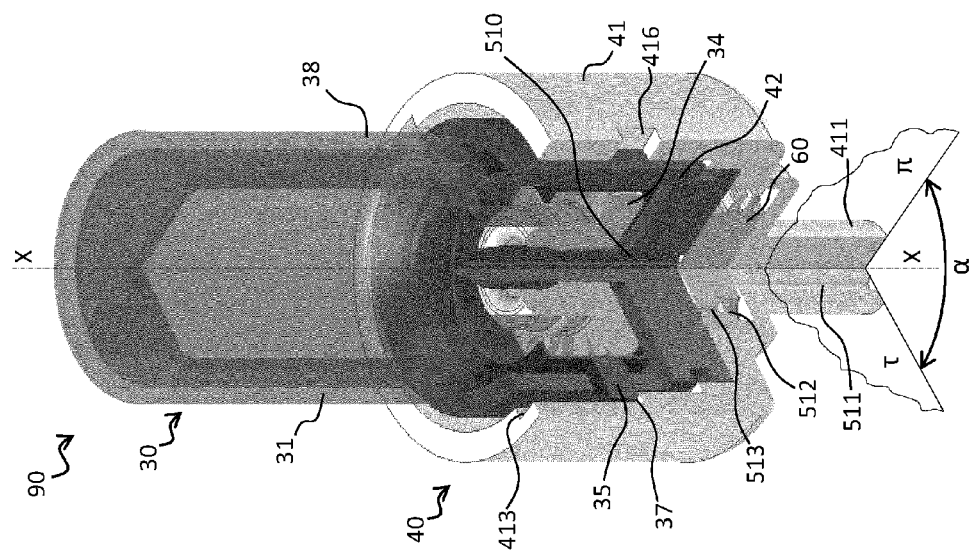
Fig. 13.a
Fig. 13.b

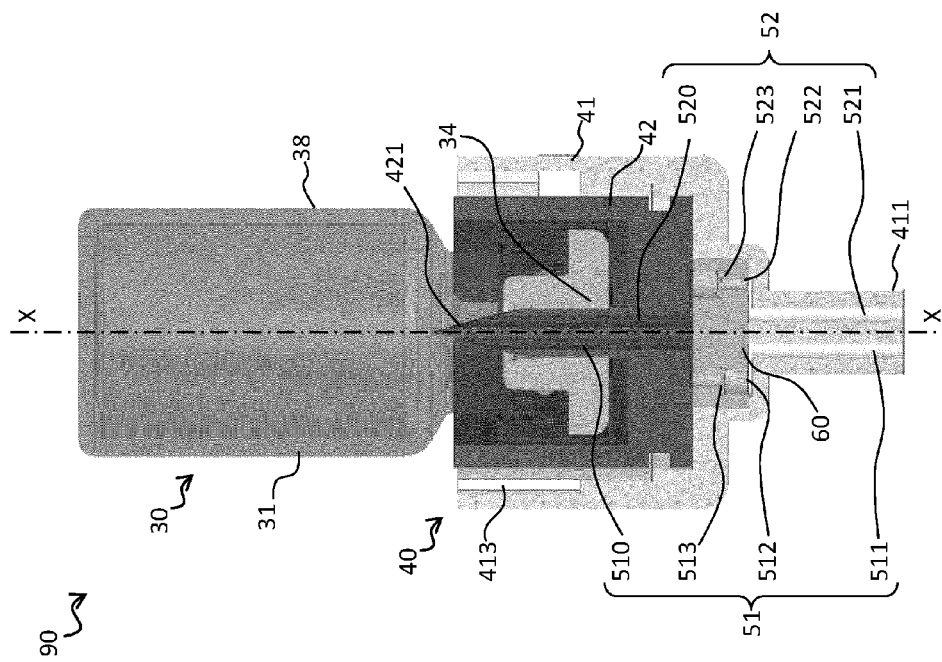
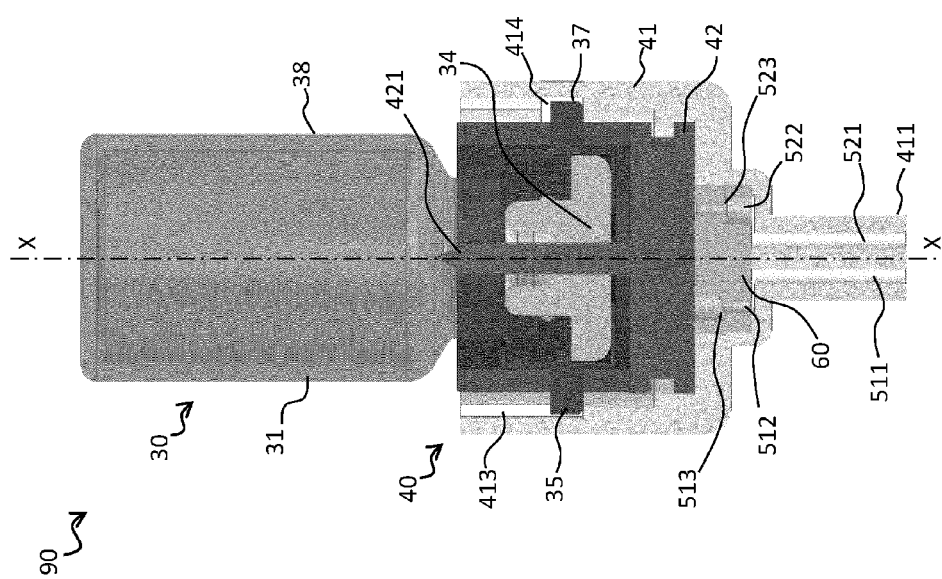

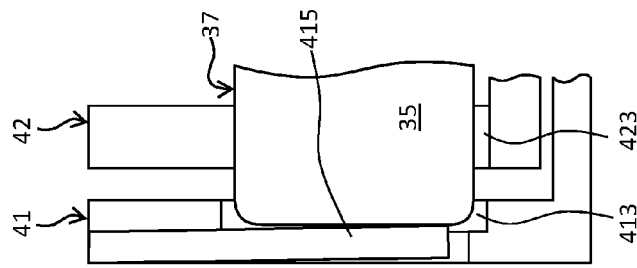
Fig. 18.a
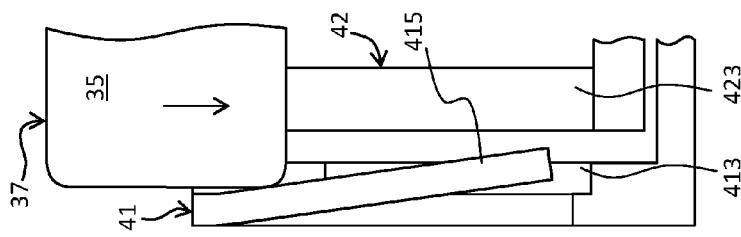
Fig. 18.b
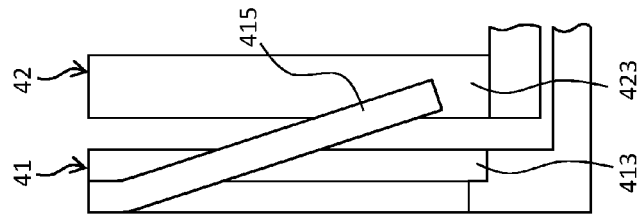
Fig. 18.c
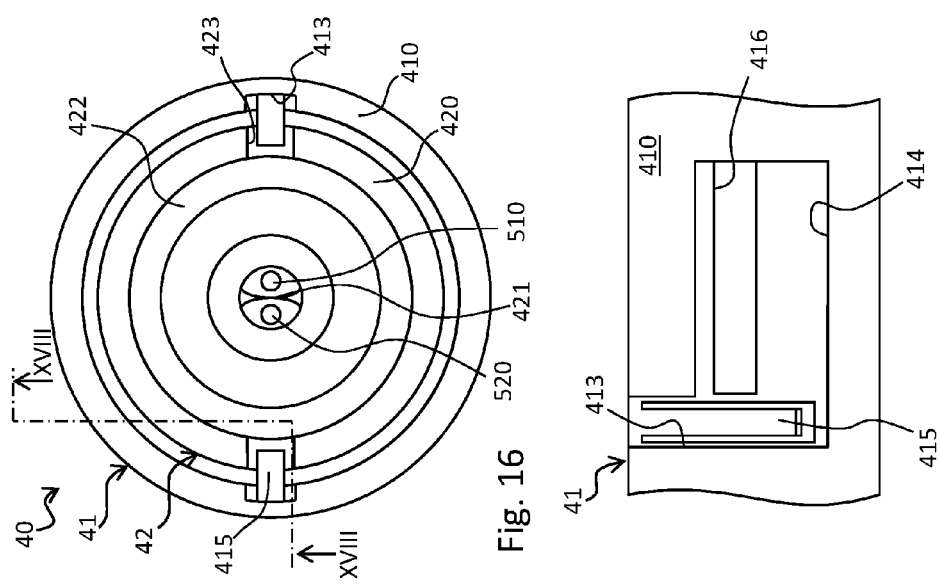
Fig. 16
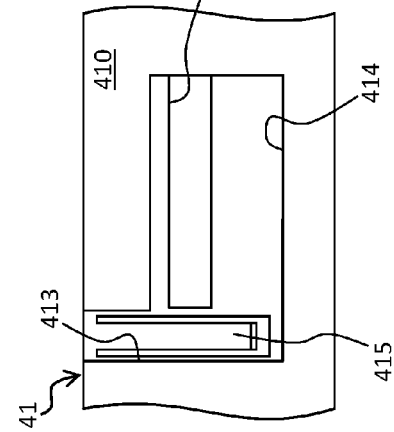
Fig. 17

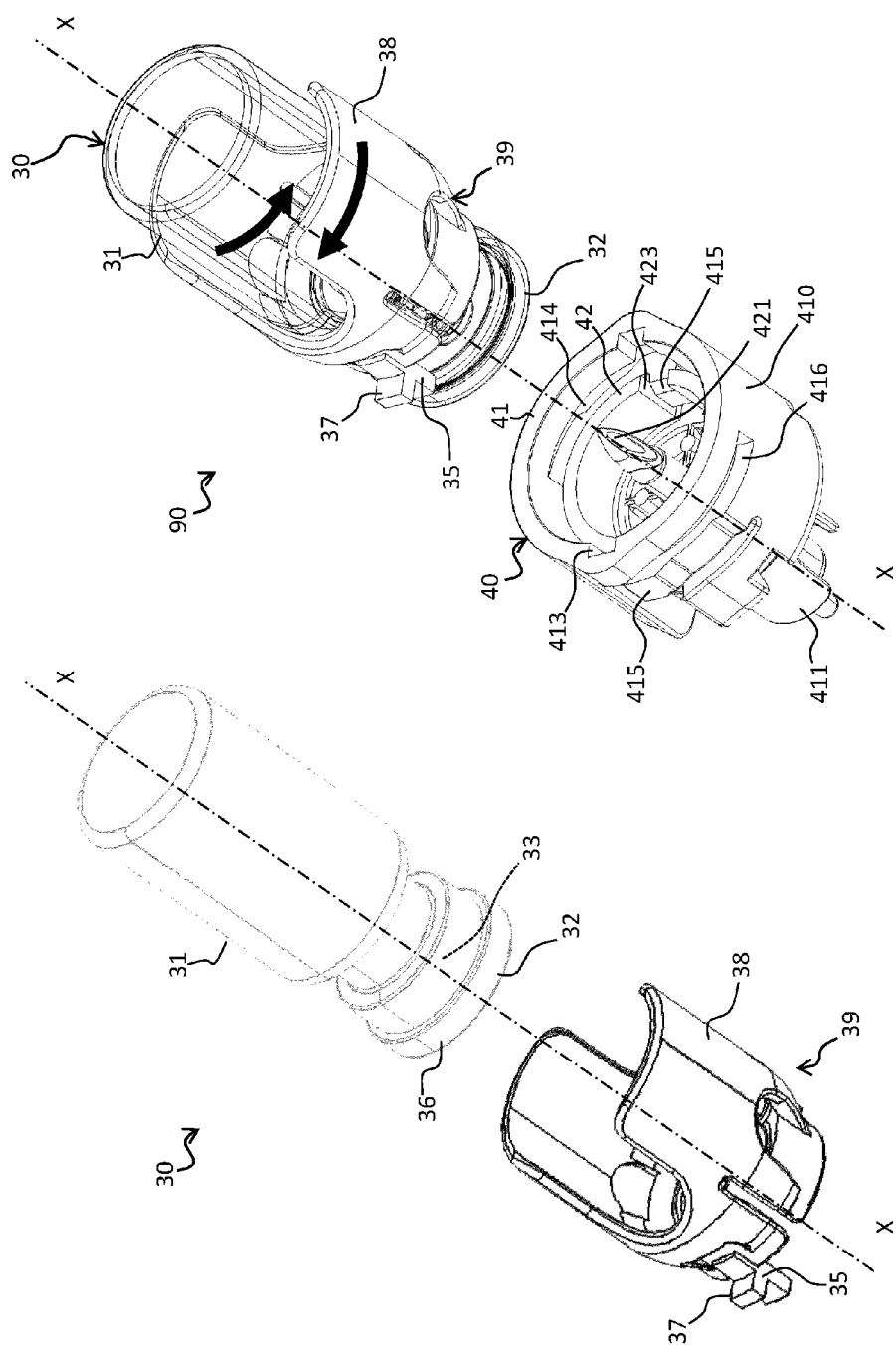

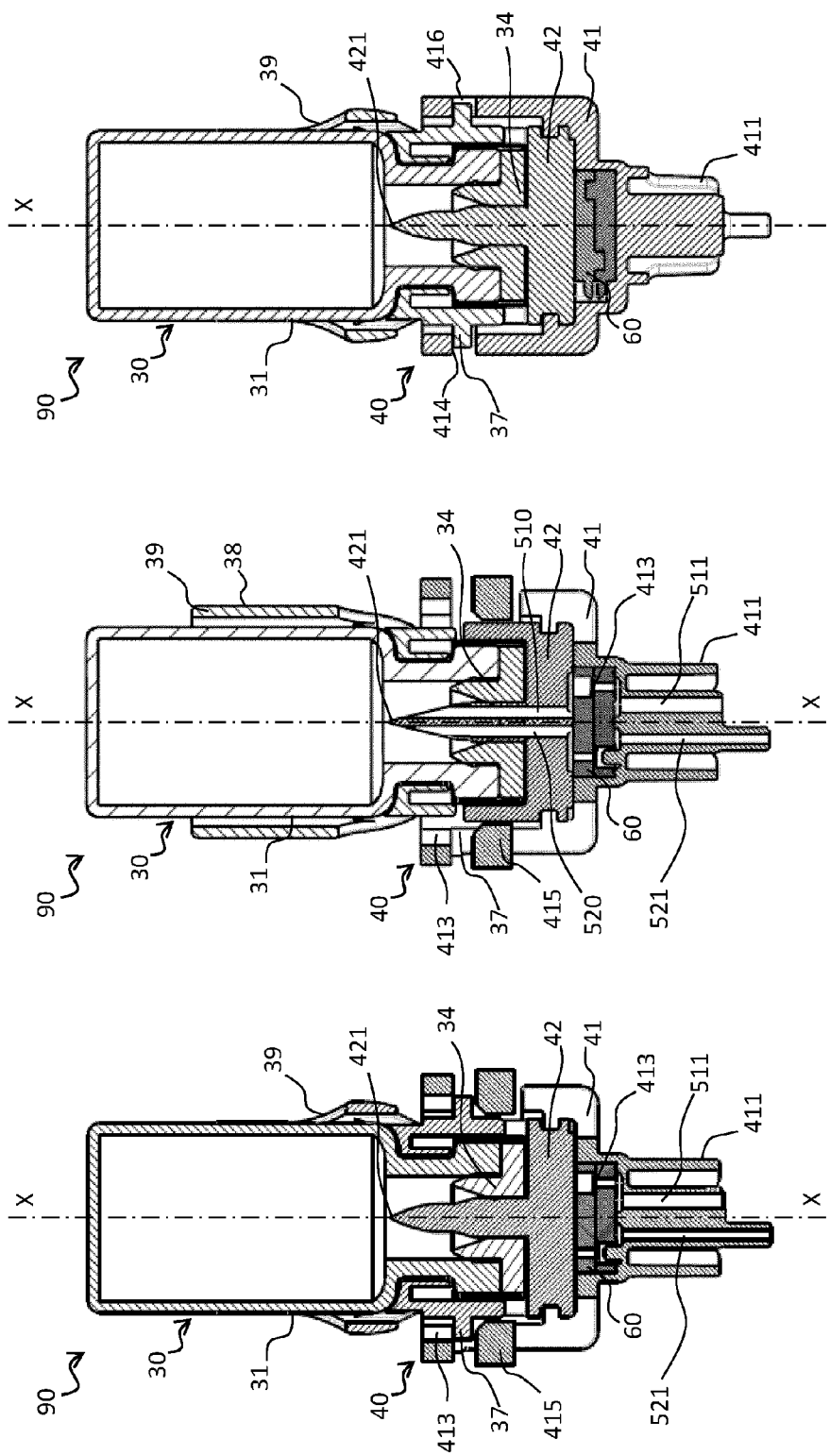

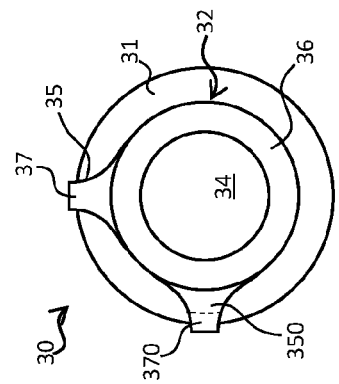
Fig. 24.c
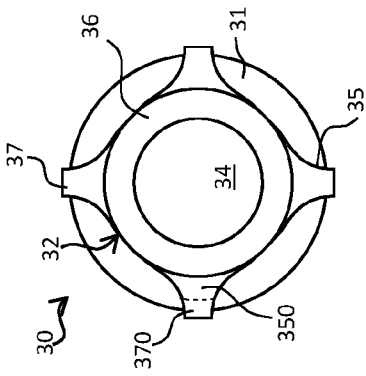
Fig. 24.a
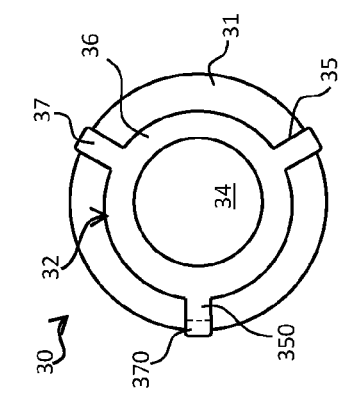
Fig. 24.b
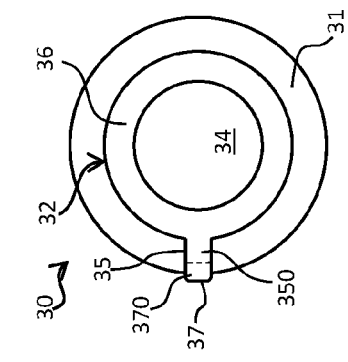
Fig. 24.d
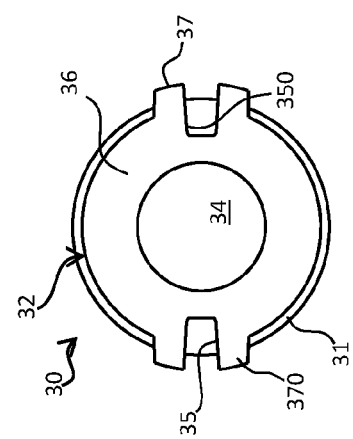
Fig. 24.e
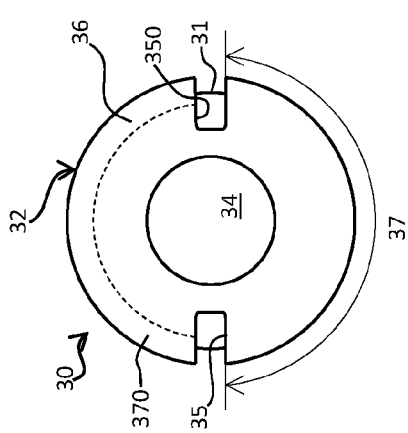
Fig. 24.f

INSERT AND VIAL FOR THE INFUSION OF LIQUIDS

This is a national stage of PCT/EP11/071,452 filed Dec. 1, 2011 and published in English, claiming the U.S. priority of 61/457,024 filed Dec. 10, 2010, which has a priority of Europe no. 10194465.0 filed Dec. 10, 2010, hereby incorporated by reference.

DESCRIPTION

The invention relates to an insert and the related vial for the transfer of liquids, for example for the infusion of drugs. Typical uses are the infusion of a drug in a circuit or in an infusion line, or more generally the transfer of the liquid from the vial to another receptacle. The invention relates also to a method for using the insert and the related vial.

There are several circumstances in which transfer of a liquid is required from a vial to another receptacle. Such circumstances may occur, for example, during therapeutic treatments like intravenous therapy or when a liquid needs to be transferred from a vial to another container, e.g. in order to dilute it. In the following description, specific reference is made to a very important field where liquids need to be transferred from a vial to a circuit or to an infusion line, i.e. the field of therapeutic treatments carried out by means of an extra-corporeal circuit, in particular a hemodialysis circuit. Such reference has no limiting intent, since the invention can be effectively used in many other fields.

During therapeutic treatments which require an extra-corporeal circulation it is often required to administer various drugs to the patient. The presence of the extra-corporeal circuit advantageously avoids the need to administer the drug by means of an injection performed directly on the patient.

By way of example hemodialysis treatment is considered below, without the scope of the invention being limited to this specific application.

During hemodialysis it is often required to administer various drugs or therapeutic substances, such as iron, heparin, erythropoietin, antibiotics and vitamins. The infusion of such substances into the extra-corporeal circuit is at present performed by means of conventional syringes. The substance is drawn from the vial in which it is supplied by the manufacturer and is then injected into a special insert provided along the circuit and equipped with a piercable cap. This known solution is schematically shown in the left portion of FIG. 2. A double transfer of the substance is therefore performed: first from the vial into the syringe and then from the syringe into the circuit.

This operation thus requires the use of disposable materials, such as the syringe and the respective needle, merely in order to transfer the substance from the vial into the circuit. Moreover, the use of needles always involves the risk of the operating staff being pricked.

Moreover, some of the substances mentioned above must be administered slowly over a period of a some minutes. It can therefore be easily understood how the administration of various substances to more than one patient represents a considerable amount of work for the nursing staff responsible for the hemodialysis treatment.

Assemblies for the infusion of substances in an extra-corporeal circuit are described for example in detail in the documents WO86/01712 and WO2007/149960.

The object of the present invention is therefore to solve at least partially the problems mentioned in connection with the infusion inserts and vials of the known types. The present invention is suitable to be combined with the invention described in the application PCT/EP2010/066056 which is hereby incorporated by reference.

One task of the present invention is to provide an insert which allows direct engagement of the related vial in which the drug is supplied, so as to avoid a double transfer of the substance.

Another task of the present invention is to provide an insert and a vial which avoid the use of conventional syringes and of the associated needles.

Another task of the present intention is to provide an insert which opens the circuit only when a proper vial is connected to it and which, on the other hand, closes the circuit again upon removal of the vial.

Another task of the present invention is to provide an insert and a vial which are adapted to avoid contamination and to enhance sterility of the overall circuit.

Another task of the present invention is provide an insert and a vial in which the vial is facilitated to convey rotational movement to the insert to improve the handling of shifting from an open to a closed configuration and vice versa.

The abovementioned object and tasks are achieved by a vial according to claim 1, by an infusion insert according to claim 5 and by a method according to claim 18.

The characteristic features and further advantages of the invention will emerge from the description provided hereinbelow, of a number of examples of embodiment, provided purely by way of a non-limiting example, with reference to the accompanying drawings in which.

Figure 4:
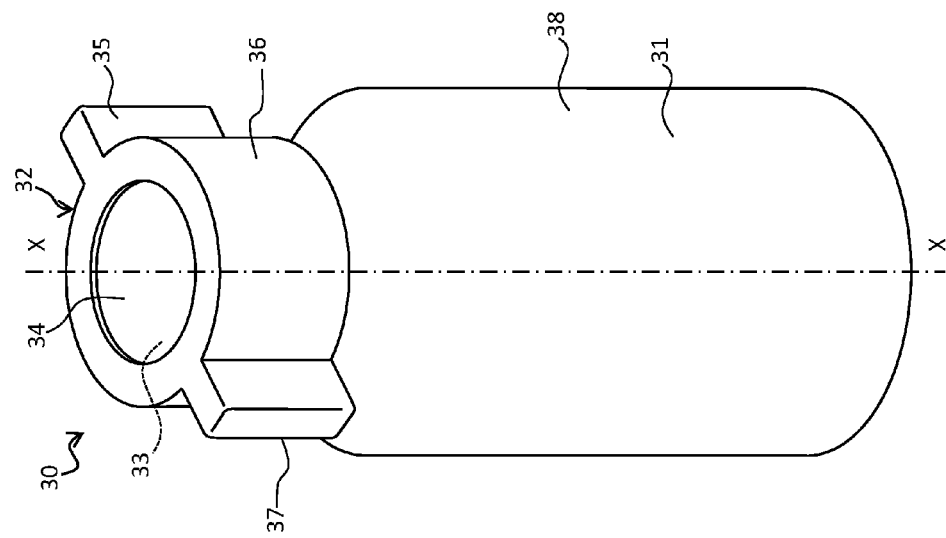
FIG. 4 shows schematically a vial for the infusion of liquids according to the invention.
Figure 3:
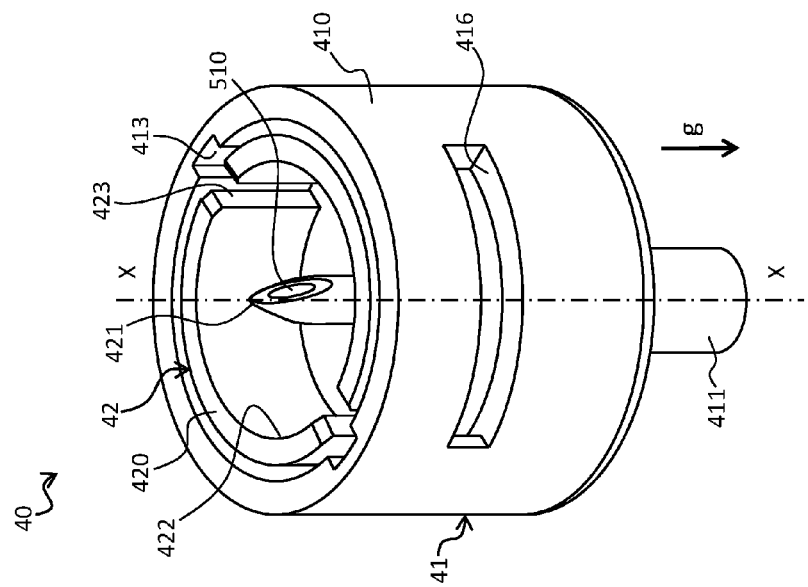
FIG. 3 shows schematically the detail, indicated by III in FIGS. 1 and 2, of the insert for the infusion of liquids according to the invention.
Figure 7:
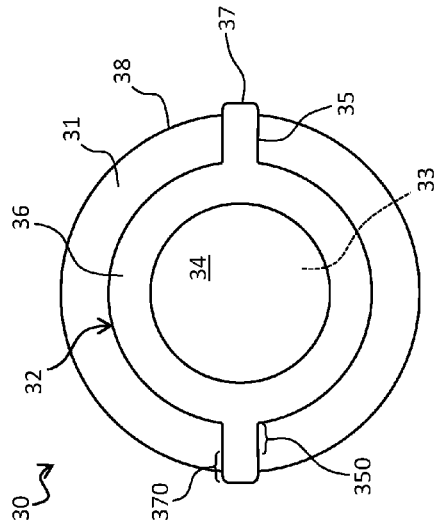
Figure 9:
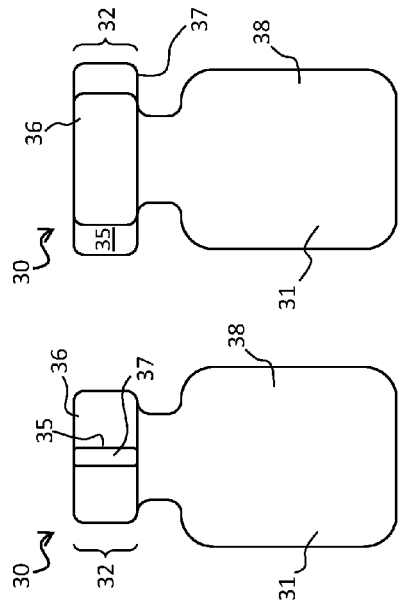
Figure 8:
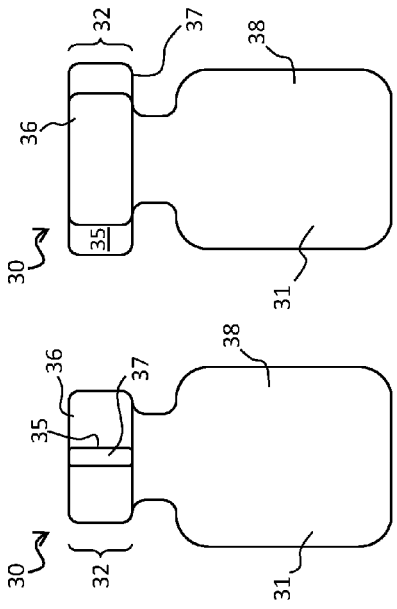
Figure 5:
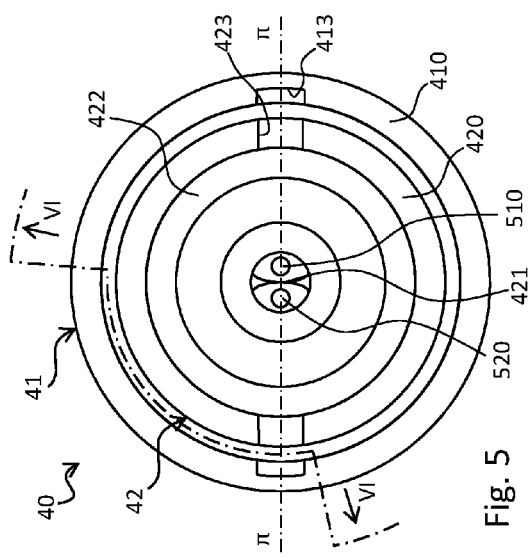
Figure 6:
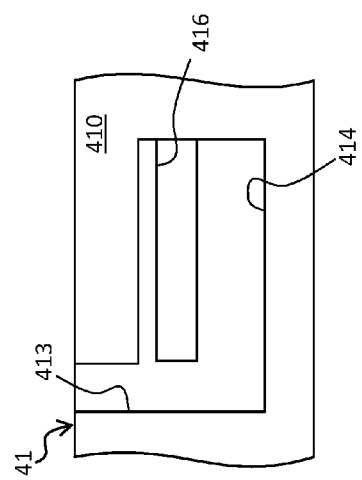

FIG. 5 schematically shows a plan view of the insert of FIG. 3;

FIG. 6 schematically shows a plane development of the cross-sectional view along the line VI-VI of FIG. 5;

FIG. 7 schematically shows a plan view of the vial of FIG. 4;

FIG. 8 schematically shows a side view of the vial of FIG. 4;

FIG. 9 schematically shows a front view of the vial of FIG. 4;

FIG. 10 shows a perspective view of an assembly according to the invention, comprising a vial connected on an insert, in a fluidly closed configuration;

FIG. 11 shows the assembly of FIG. 10 in a fluidly open configuration,

FIG. 12.*a* shows a partly cross-sectional view of the assembly of FIG. 10;

FIG. 12.*b* shows a plan scheme of the ducts of the insert in the configuration of FIG. 12.*a;*

FIG. 13.*a* shows a partly cross-sectional view of the assembly of FIG. 11;

FIG. 13.*b* shows a plan scheme of the ducts of the insert in the configuration of FIG. 12.*a;*

FIG. 14 shows a side cross-sectional view of the assembly of FIG. 10;

FIG. 15 shows a side cross-sectional view of the assembly of FIG. 11;

FIG. 16 schematically shows a plan view of an insert according to the invention similar to the one of FIG. 3;

FIG. 17 schematically shows a plane development of a cross-sectional view, similar to the one FIG. 5, of the insert of FIG. 16;

FIG. 18.*a* schematically shows the cross-sectional view along the line XVIII-XVIII of FIG. 16 in a first use configuration;

FIG. 18.*b* schematically shows the cross-sectional view along the line XVIII-XVIII of FIG. 16 in a second use configuration;

FIG. 18.*c* schematically shows the cross-sectional view along the line XVIII-XVIII of FIG. 16 in a third use configuration;

FIG. 19 shows a perspective partly exploded view of a vial according to the invention;

FIG. 20 shows a perspective view of a vial and of an insert according to the invention;

FIG. 21 shows a cross-sectional view similar to the one of FIG. 14;

FIG. 22 shows a cross-sectional view similar to the one of FIG. 15;

FIG. 23 shows a cross-sectional view perpendicular to the one of FIG. 22; and

FIG. 24.*a* schematically shows a plan view, similar to the one of FIG. 7, of a different embodiment of the vial according to the invention;

FIG. 24.*b* schematically shows a plan view, similar to the one of FIG. 7, of a different embodiment of the vial according to the invention;

FIG. 24.*c* schematically shows a plan view, similar to the one of FIG. 7, of a different embodiment of the vial according to the invention;

FIG. 24.*d* schematically shows a plan view, similar to the one of FIG. 7, of a different embodiment of the vial according to the invention;

FIG. 24.*e* schematically shows a plan view, similar to the one of FIG. 7, of a different embodiment of the vial according to the invention;

FIG. 24.*f* schematically shows a plan view, similar to the one of FIG. 7, of a different embodiment of the vial according to the invention.

The present invention relates to a vial 30 and to an insert 40 for the delivery of liquids. The vial 30 according to the invention is suitable for storing and delivering the liquid 80. The vial 30 comprises a hollow body 31 for storing the liquid 80, a grasp portion 38 and a head 32. The head 32 of the vial 30 comprises:
 a delivery opening 33 defining an axis X,
 a closing septum 34 suitable for closing the delivery opening 33; and
 at least one circumferential push surface 35 defined next to the head 32 by a protrusion 37.

The circumferential push surface 35 is firmly connected to the grasp portion 38. The insert 40 according to the invention is suitable to delivery the liquid 80 and to receive the insertion along axis X of the vial 30 disclosed above. The insert 40 comprises a main body 41 and an inner part 42. The main body 41 comprises a lateral wall 410 and a lower delivery portion 411 defining a first lower duct 511 and a second lower duct 521.

The inner part 42 of the insert 40 comprises an inner wall 420 and a piercing spike 421. The inner wall 420 defines a seat 422 suitable to receive the head 32 of the vial 30, and comprises at least one slit 423 suitable to engage a radially inner portion 350 of the at least one circumferential push surface 35 of the vial 30.

The piercing spike 421 is suitable to pierce the closing septum 34 of the vial 30 and defines a first upper duct 510 and a second upper duct 520.

The inner part 42 is housed inside the main body 41 so as to be able to rotate with respect to the latter around axis X. In particular, the inner part 42 is able to rotate between:
 a fluidly open configuration A wherein the upper ducts 510 and 520 are in fluid communication with the lower ducts 511 and 521 respectively; and
 a fluidly closed configuration B wherein the upper ducts 510 and 520 are not in fluid communication with the lower ducts 511 and 521 respectively.

Here and below reference is made to axis X both with respect to the vial 30 and with respect to the insert 40. Firstly, it has to be noticed that the two different axes will coincide in one axis X only, as soon as the vial 30 and the insert 40 are brought in the relative position which allows use thereof, i.e. in the relative position which allows insertion of the vial 30 in the insert 40. In view of this, no ambiguity arises from the use of one axis X only for both the elements.

Moreover, except in case of explicit contrary indication, the term "axial" refers to the direction of a straight line parallel to axis X, the term "radial" refers to the direction of a half-line having its origin on axis X and being perpendicular thereto, the term "circumferential" refers to the direction of a circumference having its centre on axis X and laying on a plane perpendicular thereto.

Furthermore, the terms "inner", "inside" and the like refer to positions relatively close to axis X, while "outer", "outside" and the like refer to positions relatively far from axis X.

Figure 1:
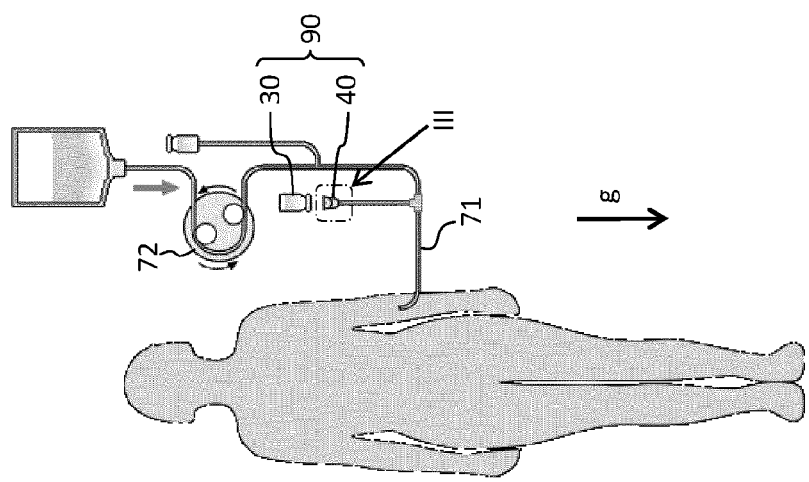
FIG. 1 shows in schematic form an infusion line used in a therapeutic treatment.

In the description of the invention, reference will be made to the spatial arrangement of the vial 30 and of the insert 40 which allows correct operation thereof. During operation of the invention, in fact, the force of gravity plays a decisive part, especially in certain embodiments. In particular, it will be assumed below that the force of gravity is directed as shown by the vector g in FIGS. 1 to 3. The vector g therefore defines the vertical direction and is oriented from the top downwards. In view of the above, the expressions "top", "upper" and the like will be used below to indicate positions which are relatively distant from the ground and, on the other hand, the expressions "bottom", "lower" and the like will be used to indicate positions relatively close to the ground.

As stated above, the circumferential push surface 35 of the vial 30 is defined by a protrusion 37. According to some embodiments, for example the one shown in FIG. 24.*d*, the protrusion 37 has a very large circumferential extension, such that the circumferential push surface 35 seems to be actually defined by a recess rather then by a protrusion 37. However, for the sake of consistency, the following description uniformly refers to the circumferential push surface 35 as defined by the protrusion 37.

The vial 30 according to the invention is similar to a common vial intended for the same use. As reported above, the vial 30 according to the invention is characterized in that it comprises at least one circumferential push surface 35. In other words, the overall shape of the head 32 of the vial 30 has no rotational symmetry. According to some embodiments, the circumferential push surface 35 is defined by a radial protrusion 37 integral with the rim of the vial 30, thus being made of the same material of the vial 30 itself, i.e. glass in most cases.

According to other embodiments, the circumferential push surface 35 is defined by a radial protrusion 37 which is part of the cover 36, known per se, intended to hold the septum 34 in place. According to the invention, the cover 36 is attached to the head 32 of the vial 30 in such a manner that a circumferential constraint is defined, i.e. that no relative rotation is allowed between them. The cover 36 can be attached to the head 32 of the vial 30 by means of crimping, moulding, gluing or a by a combination thereof. In such cases the cover 36 and the protrusion 37 integral therewith can be obtained from aluminum (Al) or from a rigid polymer such as, for example, polycarbonate (PC), polypropylene (PP), polyethylene (PE), polystyrene (PS), polyvinyl chloride (PVC), polyethylene terephthalate (PET), polybutylene terephthalate (PBT), acrylonitrile-butadiene-styrene (ABS), copolyesters or some other rigid polymer suitable for medical use.

If the rim of the vial 30 is non-circular, the shape coupling between the cover 36 and the head 32 makes it easy to obtain an effective circumferential constraint. On the contrary, if the rim of the vial 30 is a common circular one, particular attention has to be paid on the circumferential constraint between the cover 36 and the head 32 of the vial 30.

According to the above embodiments of the invention, the grasp portion 38 is part of the body 31 of the vial 30.

In other embodiments, for example those shown in FIGS. 19 to 23, the vial 30 is a standard vial modified by the attachment of a clip 39 (see FIG. 19). In particular, the clip 39 can be preferably attached to the vial 30 by means of a simple snap fit. The junction between the vial 30 and the clip 39 is preferably non-removable one. The clip 39 covers at least part of the body 31 and of the head 32 of the vial 30. The part of the clip 39 covering the head 32 of the vial 30 comprises the at least one protrusion 37 defining the circumferential push surface 35. Moreover, the part of the clip 39 covering the body 31 defines the grasp portion 38.

Accordingly, in the latter case, while an axial constraint is needed, an effective circumferential restraint is not strictly necessary between the vial 30 and the clip 39 (see FIG. 20). This embodiment offers great advantages over the previously mentioned embodiments since it allows an easier use of standard vials. As a matter of fact, since no firm circumferential restraint between vial 30 and protrusion 37 needs to be established, ordinary vials with a circular rim can be successfully used.

The above solutions which can use standard mass-produced vials for putting the invention into practice, have evident benefits in terms of costs. For example, the vial 30 can be preferably in accordance to standard DIN/ISO 8362-1, more preferably of the 2R or 4R type.

In any case, the diameter of the vial head 32 is preferably 13 mm. The seat 422 defined by the inner part 42 must match with the head 32 of the standard vial 30 or any extensions thereof, i.e. a modified cover or an attached clip.

According to some embodiments of the invention, the vial 30 comprises more than one circumferential push surface 35. For example in the embodiments shown in the attached FIGS. 4 and 7 to 9, the vial 30 comprises two symmetrical protrusions 37 each of them defining a circumferential push surface 35. In FIG. 24 other possible embodiments are shown having one protrusion only (FIG. 24.a), three protrusions (FIG. 24.b), or more protrusions (FIG. 24.c). As already stated above, the circumferential push surface 35, other than by a protrusion 37, can be defined also by a recess (see for example the embodiment of FIG. 24.d) or partly by a recess and partly by a protrusion 37 (FIG. 24.e). Moreover, as already stated above, the head 32 of the vial 30 according to the invention needs to have no rotational symmetry, while there is no need about central symmetry (see for example the embodiment of FIG. 24.f).

According to some embodiments, for example those of FIGS. 4, 7 to 9, 19, 20 24.a, 24.b, 24.d and 24.e, the circumferential push surface 35 is almost flat and parallel to the plane defined by the axial and radial directions. According to some other embodiments, for example those of FIGS. 24.c and 24.f, the circumferential push surface 35 is not flat and parallel to the axial direction. According to some further embodiments, not shown in the attached figures, the circumferential push surface 35 may have other spatial developments, the important technical feature being the possibility to transmit a push in the circumferential direction.

In view of the above, all the embodiments of FIG. 24 are suitable for putting the invention into practice. However a wide angular distance between the protrusions 37 is advisable in view of the operating principle of the invention which is described in detail below.

According to some embodiments of the insert 40, the lateral wall 410 of the main body 41 defines:
  at least one slot 413 parallel to axis X and suitable to receive a radially outer part 370 of the at least one protrusion 37 of the vial 30; and
  a circumferential rail 414 suitable to allow rotation around axis X of the at least one protrusion 37 and suitable to define a constraint in the axial direction for the same protrusion 37.

According to some embodiments of the insert 40, in the fluidly closed configuration A, the at least one slit 423 of the inner part 42 is aligned with the at least one slot 413 of the main body 41, so as to allow insertion and extraction of the at least one protrusion 37 of the vial 30. Conversely, in the fluidly open configuration B, the at least one slit 423 of the inner part 42 is not aligned with the at least one slot 413 of the main body 41, so as to avoid insertion and extraction of the at least one protrusion 37.

The piercing spike 421 is rigid and pointed at its top end. In this way it is suitable for easily perforating the septum 34 which is usually arranged on the vials 30 containing substances for therapeutic use. The piercing spike 421 extends mainly along axis X.

According to the embodiments shown in the enclosed figures, the piercing spike 421 has a monolithic structure defining both the upper ducts 510 and 520. According to some other embodiments, not shown, the piercing spike 421 has different structures, e.g. it can be obtained by means of two separate cannulas or needles, each of them defining only one of the upper ducts 510 or 520.

The upper ducts 510 and 520 extend along the piercing spike 421 preferably parallel to each other and to the axis X (see for example FIG. 15). More preferably the upper ducts 510 and 520 are symmetrically located with respect to axis X so that a plane $\pi$ comprising the axes of the upper ducts 510 and 520 also comprises axis X.

Accordingly, in order to allow fluid communication, the lower ducts 511 and 521 (or at least the upper ends thereof) have an arrangement corresponding to the one described above for the upper ducts 510 and 520. In particular, the lower ducts 511 and 521 are preferably symmetrical with respect to axis X so that a plane $\tau$ comprising the axes of the lower ducts 511 and 521 also comprises axis X.

According to these embodiments of the invention, in the fluidly closed configuration B planes $\pi$ and $\tau$ are perpendicularly intersecting along axis X (see FIGS. 12.a and 12.b), while in the fluidly open configuration A planes $\pi$ and $\tau$ coincide (see FIGS. 13.a and 13.b).

In the following, for the sake of simplicity, the complete channel obtained by the sum of the first upper duct 510 and of the first lower duct 511 is referenced to as first lumen 51. Likewise, the complete channel obtained by the sum of the second upper duct 520 and of the second lower duct 521 is referenced to as second lumen 52.

As already disclosed above, the inner part 42 is housed inside the main body 41 so as to be able to rotate with respect to the latter around axis X and so as to be constrained in the axial and radial directions. The relative rotation is preferably limited to the arch α which is needed to establish the optimal fluid communication between the upper ducts 510, 520 and the lower ducts 511, 521 (see again FIGS. 12 and 13). Preferably, the upper ducts and the lower ducts are so arranged that arch α measures 90° in width. Preferably, at the stop of the circumferential path of the protrusion 37 in the rail 414, a window 416 is provided allowing a visual check of the actual position of the protrusion 37. To enhance the visual check by the user, most of the circumferential rail 414 or even the whole circumferential rail 414 may be provided in form of a window 416.

In accordance with some embodiments, the whole insert 40, i.e. both the main body 41 and the inner part 42, is made of a rigid material, preferably a rigid polymer. Polymers which are suitable for such use are for example: polycarbonate (PC), polypropylene (PP), polyethylene (PE), polystyrene (PS), polyvinyl chloride (PVC), polyethylene terephthalate (PET), polybutylene terephthalate (PBT), acrylonitrile-butadiene-styrene (ABS), and copolyesters.

In accordance with some embodiments, e.g. those shown in the accompanying FIGS. 12 to 15, the insert 40 further comprises a resilient element 60 interposed between the main body 41 and the inner part 42 and intended to perform a seal function. In the following description and attached figures, the resilient element 60 is intended as being comprised in the main body 41. However no problem would arise from considering it as being comprised in the inner part 42. According to such embodiments, the inner part 42 is housed in the main body 41 with a slight axial interference so as to obtain a slight compression on the resilient element 60. The use of the resilient element 60 is advantageous in order to let the insert 40 work properly. The seal function makes it easier to avoid leakages of liquid 80 in the outer environment, both in the fluidly closed configuration B and in the fluidly open configuration A.

In accordance with some embodiments of the invention, the resilient element 60 and the main body 41 (or the inner part 42) are manufactured by means of two-component injection moulding. According to two-component injection moulding, in a manner known per se, the first melt (intended to originate the rigid polymer after polymerization) and the second melt (intended to originate the elastomer after polymerization) are fed, one after the other or simultaneously, into one single mould.

In accordance with some other embodiments of the invention, the resilient element 60 and the main body 41 (or the inner part 42) are manufactured separately and then assembled subsequently.

The resilient element 60 is preferably made of an elastic material, more preferably of an elastomer. Elastomers which are suitable for such use are for example: Silicone Rubber, Styrene-Ethylene-Butylene-Styrene (SEBS), Styrene-Ethylene-Propylene-Styrene (SEPS), Styrene-Isoprene-Styrene (SIS), Styrene-Butadiene-Styrene (SBS), Poly-Urethane (PU), Natural Rubber (NR) and latex.

The resilient element 60 defines intermediate ducts 512, 522 suitable to allow, in the fluidly open configuration B, the fluid communication between the upper ducts 510, 520 and the lower ducts 511, 521 respectively.

In accordance with some embodiments, the resilient element 60 defines also one one-way valve 513 or, preferably, two one-way valves 513 and 523 placed along the intermediate ducts 512, 522.

In their general embodiment, the two lumina 51 and 52 defined by the sum of the ducts in the spike 421, in the main body 41 and, if present, in the resilient element 60, are perfectly identical. However, during operation of the invention, one lumen will operate as a delivery lumen, i.e. a lumen suitable for delivering the liquid 80 from the vial 30 to the outside, while the other lumen will operate as a vent lumen, i.e. a lumen suitable for providing a replacement fluid inside the vial 30 in order to replace the delivered liquid 80. In the general embodiment each of the two lumina 51 and 52 can perform any of the functions. The presence of at least one one-way valve along one lumen clearly defines the function of both the lumina.

For example, FIGS. 14-15 and 21-22 show one-way valves placed along both the intermediate ducts 512 and 522. The one-way valve 513 placed along the first lumen 51 allows fluids to flow only upwards, while the one-way valve 523 placed along the second lumen 52 allows fluids to flow only downwards. Accordingly, in this embodiment, the first lumen 51 is definitely the vent lumen and the second lumen 52 is definitely the delivery lumen.

The presence of the one-way valve 513 allows exploiting the pulsating pressure provided in the circuit 70 by the pump 72 in order to deliver the liquid 80 contained in the vial. Both peristaltic pumps and membrane pumps, usually used in extra-corporeal circuits and medical liquid delivery lines, generate a pulsating pressure, i.e. a variable pressure oscillating about a medium value. Operation of an insert with one-way valve(s) is disclosed in depth in the European Patent Application number EP 10 162845.1 filed on May 14, 2010 by the same applicant. With reference to the accompanying figures, the operating principle of the insert 40 according to the invention is now described.

FIGS. 3, 5, 10, 12, 14 and 21 show an insert 40 according to the invention in the fluidly closed configuration B. In this configuration B, the upper ducts 510, 520 defined by the spike 421 are closed off by the upper wall of the main body 41 or preferably, if present, by the resilient element 60. Moreover, the lower ducts 511 and 521 defined by the delivery portion 411 of the main body 41 are closed off by the lower wall of the inner part 42.

FIGS. 11, 13, 15 and 22 show an insert 40 according to the invention in the fluidly open configuration A. In this configuration, upper ducts 510, 520 defined by the spike 421 are in fluid communication with the lower ducts 511 and 521 defined by the delivery portion 411 of the main body 41. Preferably, this fluid communication occurs through the intermediate ducts 512 and 522 defined by the resilient element 60.

Due to the particular structure of the ducts (especially of the intermediate ducts 512, 522), the actual presence of a fluid communication between the upper ducts 510, 520 and the lower ducts 511, 521 is not evident from the enclosed figures; such fluid communication can be hardly seen in FIGS. 12.a, 13.a, 14, 15 and 22. The transition from the fluidly closed configuration B into the fluidly open configuration A is obtained by means of engagement of a vial 30 on the insert 40. In particular, when a user presses the septum 34 of the vial 30 against the spike 421, the septum 34 itself is perforated. In this way the spike 421 penetrates inside the vial 30, connecting it with the upper ducts 510 and 520.

Further insertion of the vial 30 on the insert 40 is allowed only if the protrusion 37 is in line with the slit 423 provided on the inner part 42 and with the slot 413 provided on the main body 41. In this respect it should be noted here that, as stated above, in the fluidly closed configuration B the slit 423 and the slot 413 are aligned each other. Further insertion of the vial 30 on the insert 40 introduces the head 32 of the vial 30 in its seat 422 and, at the same time, introduces the protrusion 37 in the slit 423 and in the slot 413. Insertion of the vial 30 on the insert 40 goes on until the head 32 of the vial 30 comes into axial contact with the upper wall of the inner part 42.

At this point the user has to apply a torque on the grasp portion 38 so as to let it rotate around axis X. As soon as the grasp portion 38 starts rotating, the radially inner portion 350 of the circumferential push surface 35 makes contact with the edge of the slit 423 defined in the inner wall 420 of the inner part 42. The further rotation of the grasp portion 38 drags the inner part 42 so as to rotate it as well around axis X with respect to the main body 41. Moreover, during rotation of the grasp portion 38, the radially outer portion 370 of the protrusion 37 moves along the circumferential rail 414 defined in the lateral wall 410 of the main body 41.

A rotation of the inner part 42 with respect to the main body 41 along arch α brings the upper ducts 510, 520 in fluid communication with the lower ducts 511, 521, i.e. it brings the insert 40 into the fluidly open configuration A.

When the insert 40 is in its fluidly open configuration A with the vial 30 engaged on it, liquid 80 is able to flow from the inside of the vial 30 towards the outside, typically towards the circuit 70 or an infusion line 71. At the same time, a replacement fluid is also able to flow from the outside towards the inside of the vial 30. In this way, the volume of the supplied liquid 80 is replaced inside the vial 30 by an identical volume of a replacement fluid, so as to maintain the pressure equilibrium.

It is to be noted here that, in the fluidly open configuration A, the radially outer portion 370 of the protrusion 37 is axially constrained by the circumferential rail 414, thus avoiding any possibility for the vial 30 to be removed from the insert 40 while the circuit 70 is open. Extraction of the vial 30 from the insert 40 can be performed only after having rotated its grasp portion 38 back, along a −α arch, to the insertion position. The back rotation of the grasp portion 38 drags the inner part 42 so as to bring it in its initial angular position with respect to the main body 41. Once the insert 40 is in its fluidly closed configuration B again, the radially outer portion 370 of the protrusion 37 engages the slot 413 defined in the lateral wall 410 of the main body 41. Thus, in the fluidly closed configuration B, the vial 30 can be safely removed from the insert 40, without any risk for the circuit 70 to be put into communication with the environment.

It should be noted how the insert 40, owing to its structure described above, in general is able to assume the fluidly open configuration A only when a dedicated vial 30 is present and properly connected to it. The particular structure of the insert 40 according to the invention avoids most of the risks connected with undesired opening of the circuit. As a matter of fact, inaccurate handling of the insert 40 can hardly bring it into the fluidly open configuration A since the main body 41 itself provides no possibility to change the configuration of the insert in absence of a vial 30 according to the invention. Moreover the lateral wall 410 of the main body 41 can preferably extend axially to such an extent that the inner part 42 is covered and can not be rotated unintentionally.

Moreover, owing to its structure described above, the insert 40 is also able to automatically return into the fluidly closed configuration B upon removal of the vial 30. The insert 40 according to the invention is therefore adapted to avoid contamination and to enhance sterility of the circuit 70 since it can not be brought in its fluidly open configuration A if no vial 30 is properly attached and, conversely, it is automatically brought in its fluidly closed configuration B upon removal of the vial 30.

According to some embodiments, the insert 40 further comprises means for avoiding undesired rotation of the inner part 42 with respect to the main body 41, i.e. for avoiding rotation in absence of a vial 30 properly introduced as disclosed above.

According to some embodiments, the means for avoiding undesired rotation comprise a first movable blocking element comprised in or located on the main body 41, and a second blocking element fixed to the inner part 42. When no vial 30 is inserted in the insert 40 the first movable blocking element engages with the second blocking element, thus avoiding rotation of the inner part 42 with respect to the main body 41. The first blocking element is adapted to move such that, when a vial 30 according to the invention is inserted into the insert 40, it moves into a position where it is disengaged from the second blocking element.

In a particular embodiments, for example those shown in FIGS. 16-18 and 20, the first movable blocking means comprises a cantilever spring 415 while the second blocking means are defined by the slit 423. The cantilever spring may either extend in the axial direction (see FIGS. 16-18), in the circumferential direction (see FIG. 20) or in other directions (not shown). The cantilever spring 415 is provided in correspondence with the slot 413 and radially protrudes toward the inside of the main body 41.

When the insert 40 is in its fluidly closed configuration B, the cantilever spring 415 (first blocking element) protrudes inwardly engaging the slit 423 (second blocking element) which is aligned with the slot 413 (see in particular FIGS. 16 and 18.a). In this configuration, the cantilever spring 415 results in a circumferential constraint for the inner part 42 thus preventing the latter to rotate with respect to the main body 41. Upon insertion of a dedicated vial 30 in the insert 40, the protrusion 37 presses outwardly the cantilever spring 415 so as to progressively expel it out of the slit 423 (see in particular FIG. 18.b). When the vial 30 is completely introduced in the insert 40, the cantilever spring 415 is completely expelled out of the slit 423 by the protrusion 37, thus allowing the inner part 42 to rotate with respect to the main body 41 (see in particular FIG. 18.c).

Figure 2:
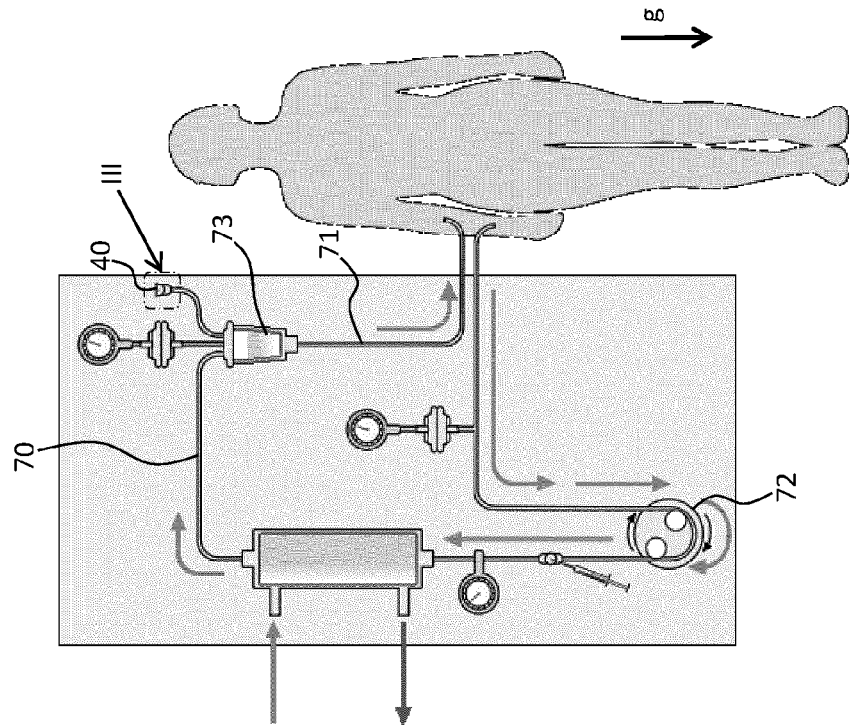
FIG. 2 shows in schematic form an extra-corporeal circuit used in a hemodialysis treatment.

The insert 40 according to the invention is preferably connected to an extra-corporeal circuit 70 in correspondence with a drip chamber 73, as per the solution shown in the FIG. 2. The drip chamber 73 is a container which allows the liquid which flows inside the extra-corporeal circuit 70 and which must be infused into the patient to drip through an air reservoir. This dripping action is intended to remove from the liquid any gas bubbles which could be dangerous for the patient. According to this embodiment, the lower ducts 511 and 521 of the main body 41 emerge inside the drip chamber 73. In this way, once the vial 30 has been connected to the insert 40 and the latter is brought into the fluidly open configuration A, liquid 80 flows down along the second lumen 52 (delivery lumen) from the vial 30 to the drip chamber 73, while air flows up along the first lumen 51 (vent lumen) from the air reservoir to the vial 30.

This operating arrangement is particularly advantageous. In fact, the same pressure present inside the circuit 70 is established inside the lumina 51, 52 and the vial 30. Thus, supplying of the liquid 80 is not affected by any pressure differences between the inside of the circuit and the external environment. Moreover, the air which enters inside the vial 30 from the circuit 70 is sterile and therefore does not risk contaminating at all the liquid 80 which is still to be supplied from the vial 30.

The use of devices for delivering a therapeutic substance directly from the vial 30 into the drip chamber are disclosed in the European patent application number EP 09 175 001.8, filed on Nov. 4, 2009 by the same applicant. Reference is made here to that previous applications for a detailed description of the drug delivery in the drip chamber, both in terms of working principles and in terms of advantages.

According to other embodiments of the insert 40, the second lower duct 521 defined by the main body 41 leads into the infusion line 71 (preferably through a drip chamber 73), while the first lower duct 511 leads into an external gas reservoir, potentially the external environment. In this way, once the vial 30 has been connected to the insert 40 and the latter is brought into its fluidly open configuration A, liquid 80 flows down inside the second lower duct 521 (delivery lumen) from the vial 30 to the infusion line 71, while inside the first lower duct 511 (vent lumen) gas flows up from the external gas reservoir to the vial 30.

This operating arrangement requires a number of additional features compared to the arrangements described above in which the vent lumen 511 is connected to the drip chamber 73. In fact, it is not possible to ensure beforehand that a pressure equilibrium is established inside the lumina 51, 52 and the vial 30. More precisely, it is not possible to ensure beforehand that the pressure inside the infusion line 71 or drip chamber 73 is the same or less than the atmospheric pressure present in the external environment, so as to allow actual delivery of the liquid 80 toward the infusion line 71. Conversely, if the pressure inside the infusion line 71 or drip chamber 73 is higher than the atmospheric pressure, the liquid 80 would be unproperly delivered into the external environment. Using the atmospheric environment as the external gas reservoir is therefore not feasible in all cases. Therefore in this embodiment it needs to be ensured that the pressure in the external gas reservoir is equal or greater than the pressure in the infusion line. Additional pressure may be provided to the gas reservoir by means of a pneumatic pump.

Moreover, the air which enters inside the vial 30 from the outside environment may not be sterile and therefore may risk contaminating the liquid 80 which is still to be supplied from the vial 30. This problem may be solved, in a known manner, by means of a sterile filter membrane which is arranged at the end of the duct connected to the external environment. The membrane allows only air to pass through and prevents the passage of any contaminating agents.

An embodiment, in which the insert 40 is not connected to a drip chamber 73 but is directly connected to the infusion line 71, requires a drip chamber 73 downstream of the insert 40 in order to eliminate air bubbles introduced in the infusion line 71. Alternatively, instead of the drip chamber 73, a means for preventing gas from going along the infusion line 71 can be provided, e.g. a wetted hydrophilic membrane or a gas blocking valve.

A second type of embodiments of the infusion line 71 will be now disclosed in detail. Such embodiments comprise an infusion line 71 intended to deliver a physiological liquid or solution to the patient. The infusion line 71 may be either for intravenous therapies, e.g. delivering a saline solution, or a substitution line needed on some hemodialysis machines as described in detail below.

Most of the recent hemodialysis machines are intended to perform also hemofiltration and/or hemodiafiltration treatments. Such treatments imply the removal of some waste water from the blood and, accordingly, they need also to compensate the removal by means of the addition of medical solution, i.e. the so called substitution liquid. Thus, hemofiltration machines comprise also an infusion line 71, i.e. the substitution line.

In the above cases, the insert 40 may be advantageously connected to the infusion line 71 rather than to the drip chamber 73.

According to such embodiments, the delivery lumen 52 of the insert 40 is arranged so as to deliver the drug from the vial 30 to the infusion line 71. Moreover, the vent lumen 51 also connects the vial 30 and the infusion line 71, thus providing physiological solution inside the vial 30 in order to replace the delivered drug. A possible connection of the insert 40 to the infusion line 71 comprises a double tube and a T-shaped connector similar to the one schematically shown in FIG. 1. According to such connection, both the delivery lumen 52 and the vent lumen 51 are connected to the infusion line 71 where the solution flows. Preferably, the intake of the vent lumen 51 is placed upstream the outlet of the delivery lumen 52.

As the skilled person may easily understand, the operation of this embodiments is perfectly analogous to the one described above, with the only exception that the replacement fluid is the physiological solution instead of a gas.

In accordance with one embodiment of the invention, means for regulating the liquid flow out of the vial 30 may be provided. In particular it is possible to envisage means—known per se in the sector relating to the infusion of liquids for medical use—able to vary the flow cross-section of the channel which conveys the liquid 80 from the vial 30 into the circuit 70. Some of these means are for example described in the documents U.S. Pat. No. 4,270,725 and EP 1 731 185.

The present invention also relates to a method for transferring a liquid 80 from a vial 30 to another receptacle, for example to a circuit 70 or an infusion line 71.

The method according to the invention comprises the steps of:

Providing a vial 30, according to the invention described above, containing the liquid 80 to be transferred;

Providing an insert 40, according to the invention described above, into its fluidly closed configuration B and placed on the receptacle in which the liquid 80 is to be transferred;

Positioning the vial 30 and the insert 40 in such a relative position that they share the same axis X and that the piercing spike 421 of the insert 40 faces the closing septum 34 of the vial 30;

Pressing the septum 34 against the spike 421 so that the septum 34 itself is perforated;

Putting the protrusion 37 in line with the slit 423 of the inner part 42 of the insert 40;

Introducing the head 32 of the vial 30 in its seat 422 defined by the inner part 42 until the head 32 of the vial 30 comes into axial contact with the upper wall of the inner part 42;

Applying a torque on the grasp portion 38 so as to let it rotate around axis X and such that the rotation of the grasp portion 38 drags the inner part 42 so as to rotate it as well around axis X with respect to the main body 41; and Continuing rotation of the grasp portion 38 and of the inner part 42 with respect to the main body 41 along arch α so as to bring the insert 40 into its fluidly open configuration A.

According to some embodiments of the invention, the method further comprises the step of putting the protrusion 37 in line both with the slit 423 of the inner part 42 and with the slot 413 of the main body 41 of the insert 40.

The invention further relates to an assembly 90 comprising a vial 30 and an insert 40 according to the above description.

With regard to the embodiments of the vial 30 and of the insert 40 according to the invention as described above, the person skilled in the art may, in order to satisfy specific requirements, may make modifications to and/or replace parts described with equivalent parts, without thereby departing from the scope of the accompanying claims.

The invention claimed is:

1. Insert (40) for the delivery of a liquid (80), suitable for receiving the insertion along an axis X of a vial (30) for storing and delivering the liquid (80), comprising a hollow body (31) for storing the liquid (80), a grasp portion (38) and a head (32) comprising: a delivery opening (33) defining an axis X, a closing septum (34) suitable for closing the delivery opening (33); and at least one circumferential push surface (35) defined next to the head (32) by a protrusion (37), the circumferential push surface (35) being firmly connected to the grasp portion (38), the insert (40) comprising a main body (41) and an inner part (42), the main body (41) comprising a lateral wall (410) and a lower delivery portion (411), the lower delivery portion (411) defining a first lower duct (511) and a second lower duct (521);

the inner part (42) comprising an inner wall (420) and a piercing spike (421);

the inner wall (420):

Defining a seat (422) suitable to receive the head (32) of the vial (30), and Comprising at least one slit (423) suitable to engage a radially inner portion (350) of the at least one circumferential push surface (35) of the vial (30);

the piercing spike (421) being suitable to pierce the closing septum (34) of the vial (30) and defining a first upper duct (510) and a second upper duct (520);

wherein the inner part (42) is housed inside the main body (41) so as to be able to rotate with respect to the latter around axis X between a fluidly open configuration A wherein the upper ducts (510, 520) are in fluid communication with the lower ducts (511, 521) respectively; and a fluidly closed configuration B wherein the upper ducts (510, 520) are not in fluid communication with the lower ducts (511, 521) respectively.

2. Insert (40) according to claim 1, wherein the lateral wall (410) defines:

at least a slot (413) parallel to axis X and suitable to receive a radially outer part (370) of the at least one protrusion (37); and a circumferential rail (414) suitable to allow rotation around axis X of the at least one protrusion (37) and suitable to define a constraint in the axial direction for the protrusion (37).

3. Insert (40) according to claim 1, wherein, in the fluidly closed configuration A, the at least one slit (423) of the inner part (42) is aligned with the at least one slot (413) of the main body (41), so as to allow insertion and extraction of the at least one protrusion (37) of the vial (30), while in the fluidly open configuration B, the at least one slit (423) of the inner part (42) is not aligned with the at least one slot (413) of the main body (41), so as to avoid insertion and extraction of the at least one protrusion (37).

4. Insert (40) according to claim 1 further comprising a resilient element (60) interposed between the main body (41) and the inner part (42) and intended to perform a seal function.

5. Insert (40) according to claim 4, wherein the resilient element (60) defines a first intermediate duct (512) and a second intermediate duct (522), the intermediate ducts (512, 522) being suitable to allow, in the fluidly open configuration B, the fluid communication between the upper ducts (510, 520) and the lower ducts (511, 521) respectively.

6. Insert (40) according to claim 5, wherein the resilient element (60) also defines at least one one-way valve (513).

7. Insert (40) according to claim 1, further comprising means (415) for avoiding undesired rotation of the inner part (42) with respect to the main body (41) in absence of the vial (30) properly introduced.

8. Insert (40) according to claim 7, wherein the means for avoiding undesired rotation of the inner part (42) comprise a first movable blocking element (415) comprised in or located on the main body (41), and a second blocking element (423) fixed to the inner part (42), wherein the first movable blocking element (415) engages the second blocking element (423) when no vial (30) is inserted in the insert (40) and wherein the first movable blocking element (415) is adapted to move into a position where it is disengaged from the second blocking element (423) when the vial (30) is inserted into the insert (40).

9. Insert (40) according to claim 8, wherein the first movable blocking element comprises a cantilever spring (415).

10. Insert (40) according to claim 8, wherein the second blocking element is defined by the slit (423).

11. Insert (40) according to claim 8, wherein the first movable blocking element is provided in correspondence with a slot (413) of the main body (41).

12. Insert (40) according to claim 8, wherein, in the fluidly closed configuration B, the first movable blocking element (415) radially protrudes toward the inside of the main body (41) so as to engage the second blocking element (423).

13. Assembly (90) comprising a vial (30) for storing and delivering a liquid (80), having a hollow body (31) for storing the liquid (80), a grasp portion (38) and a head (32) including:

a delivery opening (33) defining an axis X, a closing septum (34) suitable for closing the delivery opening (33);

at least one circumferential push surface (35) defined next to the head (32) by a protrusion (37), the circumferential push surface (35) being firmly connected to the grasp portion (38); and an insert (40) according to claim 5, for the delivery of the liquid (80), and suitable for receiving the insertion along an axis X of the vial (30).

14. Method for transferring a liquid (80) from a vial (30) to another receptacle, comprising the steps of:

Providing the vial (30), for storing and delivering the liquid (80), having a hollow body (31) for storing the liquid (80), a grasp portion (38) and a head (32) including:

a delivery opening (33) defining an axis X, a closing septum (34) suitable for closing the delivery opening (33); and at least one circumferential push surface (35) defined next to the head (32) by a protrusion (37), the circumferential push surface (35) being firmly connected to the grasp portion (38) and an insert (40) for the delivery of the liquid (80), suitable for receiving the insertion along an axis X of the vial (30), Providing an insert (40), according to claim 5, into its fluidly closed configuration B and placed on the receptacle in which the liquid (80) is to be transferred;

Positioning the vial (30) and the insert (40) in such a relative position that they share the same axis X and that the piercing spike (421) of the insert (40) faces the closing septum (34) of the vial (30);

Pressing the septum (34) against the spike (421) so that the septum (34) itself is perforated;

Putting the protrusion (37) in line with the slit (423) of the inner part (42) of the insert (40);

Introducing the head (32) of the vial (30) in its seat (422) defined by the inner part (42) until the head (32) of the vial (30) comes into axial contact with the upper wall of the inner part (42);

Applying a torque on the grasp portion (38) so as to let it rotate around axis X and such that the rotation of the grasp portion (38) drags the inner part (42) so as to rotate it as well around axis X with respect to the main body (41); and Continuing rotation of the grasp portion (38) and of the inner part (42) with respect to the main body (41) along an arch $\alpha$ so as to bring the insert (40) into its fluidly open configuration A.

\* \* \* \* \*